US008133475B2

(12) United States Patent
Tancredi et al.

(10) Patent No.: US 8,133,475 B2
(45) Date of Patent: Mar. 13, 2012

(54) CALCIUM PHOSPHATE COMPLEX IN ACID CONTAINING CHEWING GUM

(75) Inventors: Doris Tancredi, Sparta, NJ (US); Ding Ming, Morris Plains, NJ (US); Samantha Holme, Pompton Plains, NJ (US)

(73) Assignee: Cadbury Adams USA, LLC, Parsippany, NJ (US)

( * ) Notice: Subject to any disclaimer, the term of this patent is extended or adjusted under 35 U.S.C. 154(b) by 372 days.

(21) Appl. No.: 11/732,803

(22) Filed: Apr. 4, 2007

(65) Prior Publication Data
US 2007/0237805 A1   Oct. 11, 2007

Related U.S. Application Data

(60) Provisional application No. 60/789,528, filed on Apr. 5, 2006.

(51) Int. Cl.
*A61K 9/68* (2006.01)
(52) U.S. Cl. .......................... 424/48; 424/440
(58) Field of Classification Search ............. 424/48
See application file for complete search history.

(56) References Cited

U.S. PATENT DOCUMENTS

| | | |
|---|---|---|
| 325,711 A | 9/1885 | Stuckes |
| 605,414 A | 6/1898 | Fonteine |
| 678,044 A | 7/1901 | Scott |
| 810,210 A | 1/1906 | Laws |
| 943,945 A | 12/1909 | Liebich |
| 1,771,506 A | 7/1930 | Mustin |
| 1,771,982 A | 7/1930 | Mustin |
| 2,004,957 A | 6/1935 | Messner |
| 2,448,786 A | 9/1948 | Faxon |
| 2,589,270 A | 3/1952 | Mayle |
| 2,973,273 A | 2/1961 | Curtiss |
| 3,071,476 A | 1/1963 | Werft et al. |
| 3,795,748 A | 3/1974 | Cillario et al. |
| 3,806,290 A | 4/1974 | Graff et al. |
| 3,857,963 A | 12/1974 | Graff et al. |
| 3,894,154 A | 7/1975 | Graff et al. |
| 4,150,161 A | 4/1979 | Rudolph et al. |
| 4,156,740 A | 5/1979 | Glass et al. |
| 4,157,402 A | 6/1979 | Ogawa et al. |
| 4,224,345 A | 9/1980 | Tezuka et al. |
| 4,251,201 A | 2/1981 | Krysiak |
| 4,252,829 A | 2/1981 | Terrevazzi |
| 4,269,860 A | 5/1981 | Ogawa et al. |
| 4,271,197 A | 6/1981 | Hopkins et al. |
| 4,271,198 A | 6/1981 | Cherukuri et al. |
| 4,291,045 A | 9/1981 | Mackay et al. |
| 4,292,329 A | 9/1981 | Ogawa et al. |
| 4,301,178 A | 11/1981 | Witzel et al. |
| 4,316,915 A | 2/1982 | Friello et al. |
| 4,317,838 A | 3/1982 | Cherukuri et al. |
| 4,328,249 A | 5/1982 | Mackay et al. |
| 4,329,369 A | 5/1982 | Tezuka et al. |
| 4,352,822 A | 10/1982 | Cherukuri et al. |
| 4,352,823 A | 10/1982 | Cherukuri et al. |
| 4,352,824 A | 10/1982 | Puglia et al. |
| 4,352,825 A | 10/1982 | Cherukuri et al. |
| 4,374,858 A | 2/1983 | Glass et al. |
| 4,382,962 A | 5/1983 | Devos et al. |
| 4,399,154 A | 8/1983 | Puglia et al. |
| 4,421,773 A | 12/1983 | Akutagawa |
| 4,430,351 A | 2/1984 | Cillario |
| 4,466,983 A | 8/1984 | Cifrese et al. |
| 4,485,118 A | 11/1984 | Carroll et al. |
| 4,513,012 A | 4/1985 | Carroll et al. |
| 4,543,769 A | 10/1985 | Schmitz |
| 4,563,345 A | 1/1986 | Arrick |
| 4,601,907 A | 7/1986 | Knebl et al. |
| 4,614,654 A | 9/1986 | Ream et al. |
| 4,614,658 A | 9/1986 | Wilson et al. |
| 4,642,235 A | 2/1987 | Reed et al. |
| 4,647,450 A | 3/1987 | Peters et al. |
| 4,656,039 A | 4/1987 | Weiss et al. |
| 4,675,288 A | 6/1987 | Falck |
| 4,683,138 A | 7/1987 | Glass et al. |
| 4,707,363 A | 11/1987 | Sato et al. |
| 4,738,854 A | 4/1988 | Friello et al. |
| 4,741,905 A | 5/1988 | Huzinec |
| 4,753,806 A | 6/1988 | Carroll et al. |
| 4,762,719 A | 8/1988 | Forester |
| 4,872,884 A | 10/1989 | Cherukuri et al. |
| 4,938,128 A | 7/1990 | Knebl |
| 4,949,630 A | 8/1990 | Knebl |

(Continued)

FOREIGN PATENT DOCUMENTS

CA    2589270 A1    6/2006

(Continued)

OTHER PUBLICATIONS

"Calpis Candy—Assortment by Kanro" Japanscan; May 2000, Report 193961.
"Centres for High Boilings—Fruit Pulp, Caramel, Treacle or Powder"; By "Sweetmaker" Confectionery Production; vol. 48, pp. 344-345 (Aug. 1982).
Deis, R., "Polyols in Confectionery," Manufacturing Confectioner; vol. 80(10): 53-57 (Oct. 2000).
Fritz, Douglas P, "Using Confectionery Equipment to Manufacture Chewing Gum," Manufacturing Confectioner; vol. 80(11): 45-48 (Nov. 2000).
Gonze, M., "High Purity Erythritol for New Health Food Applications," ZFL, Internationale Zeitschrift Fur Lebensmittel• Tichnik, Marketing, Verpackung and Analytik; vol. 47(11): 66-68 (1996).

(Continued)

*Primary Examiner* — Gollamudi Kishore
*Assistant Examiner* — Snigdha Maewall
(74) *Attorney, Agent, or Firm* — Hoffmann & Baron LLP

(57) ABSTRACT

The present invention relates to chewing gum and confectionery compositions for improving the dental health of mammals, particularly humans. In particular, the compositions may include a gum base or carrier, sweetening agents, casein phosphopeptide-calcium phosphate (CPP-ACP) and food-grade acids. The compositions may be employed to remineralize the tooth surfaces of mammals, as well as impart acid resistance thereto.

22 Claims, No Drawings

U.S. PATENT DOCUMENTS

| | | |
|---|---|---|
| 4,971,806 A | 11/1990 | Cherukuri et al. |
| 4,975,288 A | 12/1990 | Hager et al. |
| 4,980,178 A | 12/1990 | Cherukuri et al. |
| 4,981,698 A | 1/1991 | Cherukuri et al. |
| 4,997,659 A | 3/1991 | Yatka et al. |
| 5,045,326 A | 9/1991 | Glass et al. |
| 5,116,626 A | 5/1992 | Synosky et al. |
| 5,125,819 A | 6/1992 | Hager et al. |
| 5,130,123 A | 7/1992 | Reynolds et al. |
| 5,139,797 A | 8/1992 | Huzinec et al. |
| 5,156,866 A | 10/1992 | Sato et al. |
| 5,227,154 A | 7/1993 | Reynolds |
| 5,244,887 A | 9/1993 | Straub |
| 5,279,842 A | 1/1994 | Escola Gallart et al. |
| 5,344,659 A | 9/1994 | Kurihara et al. |
| 5,399,365 A | 3/1995 | Yatka et al. |
| 5,425,961 A | 6/1995 | Yatka et al. |
| 5,431,929 A | 7/1995 | Yatka et al. |
| 5,458,892 A | 10/1995 | Yatka et al. |
| 5,498,429 A | 3/1996 | Orlandi et al. |
| 5,502,045 A | 3/1996 | Miettinen et al. |
| 5,525,360 A | 6/1996 | Yatka et al. |
| 5,612,070 A | 3/1997 | Yatka et al. |
| 5,626,892 A | 5/1997 | Kehoe et al. |
| 5,626,896 A | 5/1997 | Moore et al. |
| 5,637,334 A | 6/1997 | Yatka et al. |
| 5,670,163 A | 9/1997 | Cuca et al. |
| 5,672,367 A | 9/1997 | Grijpma et al. |
| 5,833,954 A * | 11/1998 | Chow et al. ............. 424/49 |
| 5,879,728 A | 3/1999 | Graff et al. |
| 5,952,019 A | 9/1999 | Yatka et al. |
| 5,955,116 A | 9/1999 | Kehoe et al. |
| 6,054,144 A | 4/2000 | Burruano et al. |
| 6,087,353 A | 7/2000 | Stewart et al. |
| 6,242,019 B1 | 6/2001 | Bell et al. |
| 6,264,999 B1 | 7/2001 | Yatka et al. |
| 6,280,762 B1 | 8/2001 | Bealin-Kelly et al. |
| 6,280,780 B1 * | 8/2001 | Degady et al. ............. 426/5 |
| 6,284,291 B1 | 9/2001 | Siecke et al. |
| 6,306,429 B1 | 10/2001 | Bealin-Kelly |
| 6,375,997 B1 | 4/2002 | Sheen et al. |
| 6,432,441 B1 | 8/2002 | Bealin-Kelly et al. |
| 6,472,001 B1 | 10/2002 | Bunkers et al. |
| 6,491,540 B1 | 12/2002 | Barreca |
| 6,528,102 B1 | 3/2003 | Coyle et al. |
| 6,551,643 B2 | 4/2003 | Bernatz et al. |
| 6,558,727 B2 | 5/2003 | Degady et al. |
| 6,562,382 B1 | 5/2003 | Corriveau et al. |
| 6,602,518 B2 | 8/2003 | Seielstad et al. |
| 6,613,346 B2 | 9/2003 | Seielstad et al. |
| 6,623,266 B2 | 9/2003 | Jani et al. |
| 6,652,839 B2 | 11/2003 | Barreca |
| 6,652,845 B2 | 11/2003 | Hu et al. |
| 6,692,778 B2 | 2/2004 | Yatka et al. |
| 6,780,844 B1 * | 8/2004 | Reynolds ............. 514/7 |
| 6,846,495 B2 | 1/2005 | Dobrozsi et al. |
| 6,846,500 B1 | 1/2005 | Luo et al. |
| 6,869,614 B2 | 3/2005 | Barreca |
| 6,949,264 B1 | 9/2005 | McGrew et al. |
| 7,108,885 B2 | 9/2006 | Serpelloni |
| 2002/0004083 A1 | 1/2002 | Yatka et al. |
| 2002/0051836 A1 | 5/2002 | Yatka et al. |
| 2002/0102333 A1 | 8/2002 | Klug et al. |
| 2002/0136812 A1 | 9/2002 | Degady et al. |
| 2002/0142059 A1 | 10/2002 | Jani et al. |
| 2002/0192330 A1 | 12/2002 | Bunkers et al. |
| 2003/0008062 A1 | 1/2003 | Day et al. |
| 2003/0059501 A1 | 3/2003 | Rivier |
| 2003/0072841 A1 | 4/2003 | Rajaiah et al. |
| 2003/0138518 A1 | 7/2003 | Kiefer et al. |
| 2003/0190397 A1 | 10/2003 | Serpelloni |
| 2003/0198713 A1 | 10/2003 | Clark et al. |
| 2004/0037788 A1 | 2/2004 | Barreca |
| 2004/0037924 A1 | 2/2004 | Jani et al. |
| 2004/0037925 A1 | 2/2004 | Jani et al. |
| 2004/0058033 A1 | 3/2004 | Sozzi et al. |
| 2004/0096544 A1 | 5/2004 | Yatka et al. |
| 2004/0126472 A1 | 7/2004 | Soldani |
| 2004/0131751 A1 | 7/2004 | Dekker et al. |
| 2004/0180110 A1 | 9/2004 | Mistry |
| 2004/0234459 A1 | 11/2004 | Faust et al. |
| 2005/0008732 A1 | 1/2005 | Gebreselassie et al. |
| 2005/0089481 A1 * | 4/2005 | Yamanaka et al. ............. 424/50 |
| 2005/0100633 A1 | 5/2005 | Bunkers et al. |
| 2005/0112236 A1 | 5/2005 | Boghani et al. |
| 2005/0170041 A1 | 8/2005 | Abraham et al. |
| 2005/0175733 A1 | 8/2005 | Thorengaard et al. |
| 2005/0260317 A1 | 11/2005 | Cotten et al. |
| 2005/0260329 A1 | 11/2005 | Yusuf et al. |
| 2006/0024354 A1 | 2/2006 | Barreca |
| 2006/0100398 A1 | 5/2006 | Shaffer et al. |
| 2006/0188612 A1 | 8/2006 | Lorenzi |
| 2007/0087100 A1 | 4/2007 | Fornaguera |
| 2007/0104828 A1 | 5/2007 | Fornaguera |
| 2007/0104830 A1 | 5/2007 | Fornaguera |
| 2007/0122528 A1 | 5/2007 | Cathenaut et al. |
| 2007/0148285 A1 | 6/2007 | Yang |
| 2007/0160707 A1 | 7/2007 | Garcia |

FOREIGN PATENT DOCUMENTS

| | | |
|---|---|---|
| CA | 2612172 A1 | 12/2006 |
| EP | 0086856 A1 | 7/1986 |
| EP | 0320580 B1 | 7/1993 |
| EP | 0806151 A2 | 11/1997 |
| EP | 1004594 A1 | 5/2000 |
| EP | 0724837 B1 | 12/2000 |
| EP | 1151673 A2 | 11/2001 |
| EP | 0944331 B1 | 3/2002 |
| EP | 1003475 B1 | 1/2004 |
| EP | 1425976 A1 | 6/2004 |
| GB | 2042969 A | 10/1980 |
| GB | 2177587 A | 1/1987 |
| JP | 1951-5888 | 9/1951 |
| JP | 04-179445 | 6/1992 |
| JP | 05-38258 A | 2/1993 |
| RU | 2239413 C1 | 11/2004 |
| WO | 9508925 A1 | 4/1995 |
| WO | 9706695 A1 | 2/1997 |
| WO | 9726798 A1 | 7/1997 |
| WO | 9824325 A1 | 6/1998 |
| WO | 9840406 A1 | 9/1998 |
| WO | 9847484 A1 | 10/1998 |
| WO | 9933352 A1 | 7/1999 |
| WO | 0006127 A1 | 2/2000 |
| WO | 0019977 A1 | 4/2000 |
| WO | 0057842 A2 | 10/2000 |
| WO | 0062762 A1 | 10/2000 |
| WO | 0167884 A1 | 9/2001 |
| WO | 02056698 A1 | 7/2002 |
| WO | 2004028266 A1 | 4/2004 |
| WO | 2005037238 A2 | 4/2005 |
| WO | 2005048728 A1 | 6/2005 |
| WO | 2005058263 A1 | 6/2005 |
| WO | 2005065461 A1 | 7/2005 |
| WO | 2006026298 A2 | 3/2006 |
| WO | 2006037319 A1 | 4/2006 |
| WO | 2006039519 A1 | 4/2006 |
| WO | 2006056013 A1 | 6/2006 |
| WO | 2006077480 A1 | 7/2006 |
| WO | 2006127618 A2 | 11/2006 |
| WO | 2007079333 A2 | 7/2007 |

OTHER PUBLICATIONS

Hintlian, F., "Filled Hard Candy," Manufacturing Confectioner; vol. 75(10): pp. 61-66 (Oct. 1995).

Honpo, Senjakuame, "Orange Pure Sherbet Candy; Lemon Pure Sherbet Candy," International Product Alert; vol. 8(21) (Nov. 1991).

International Preliminary Report on Patentability for PCT/US07/08465, mailed Sep. 12, 2008.

Kacena, Radka, "Hard Coat Panning," The Manufacturing Confectioner; pp. 41-77 (Oct. 1997).

Kanro 10 Tsubu Hinyari Suika Nodoame 10 Candy by Kanro; Jul. 2002, Report 242381.

Long, T, "Producing Centre Filled Hard Candy, Chewing Gum and Toffees," Candy and Snack Industry; vol. 145(11): 34, 37 (Nov. 1980).

Lu et al., "Direct reasons, influencing factors and preventing methods of enamel demineralization in orthodontic treatment with fixed applicances," J. Foreign Medical Sciences (Stomatology)m 2004, 31 (suppl): 167-169.

Matlow, Swizzels, "Stingers Taffy Bar—Lemon; Raspberry; Fruit Punch," Nov. 1996, Report 120966.

Mega Warheads Fruit Flavored Candy—Sour Lemon; Fruit Flavored Candy—Sour Apple; Fruit Flavored Candy—Hot Grape; Fruit Flavored Candy—Hot Cherry, by Foreign Candy Co., Inc.; Product Alert; Jun. 1991, Report No. 096490.

"Product Parade," Candy Industry; Dec. 1991, p. 10.

Reynolds, "Remineralization of Enamel Subsurface Lesions by Casein Phopsphopeptide-stabilized Calcium Phopshate Solutions," J Dent Res; 76(9): 1587-1595 (Sep. 1997).

Rogers, P; "Helping the Medicine Go Down"; vol. 166(5): 36-40 (2001).

Shen, P. et al., "Reminerilzation of enamel subsurface lesions by suar-free chewing gum containing casein phosphopeptide-amorphous calcium phosphate," J of Dental Research 80(12): 2066-2070 (2001).

Shokuhin, Kanebo; "Ninja Club"; International Product Alert, Dec. 1986, Report No. 044453.

Warner Lambert Co., "Chewels Sugarless Gum", Oct. 17, 1983, Report No. 018172, http://www. prod uctscan.com/search/full record.cfm?frprt=11085.

Warner Lambert Co., "Freshen-Up Fruit Gum", Feb. 4, 1980, Report No. 000339, http://www.productscan.com/search/fullrecord. cfm?frpt=336.

Warner Lambert Co., "Freshen-Up Peppermint Gum; Freshen-Up Fruit Gum", Aug. 23, 1982, Report No. 010075, http:||www. productscan.com/search/fullrecord.cfm?frprt=9657.

Yoshinori, Ichinose, "Emergence of Recaldent, New Anti-Caries Substrance," Dec. 1, 2002 (search conducted on Oct. 28, 2010), URL: http://keepsmile.info/cppacp.html.

McIntyre, M, "Isomalt as an International Sugar Replacer," Food Ingredients and Analysis International; 23(6): 35-36 (2001).

E.C. Reynolds., "Dairy Products and Dental Health", Proceedings of the Nutrition Society of Australia; 19: 95-102 (1995).

* cited by examiner

CALCIUM PHOSPHATE COMPLEX IN ACID CONTAINING CHEWING GUM

CROSS-REFERENCE TO RELATED APPLICATIONS

This application claims the benefit of U.S. Provisional Application No. 60/789,528, filed Apr. 5, 2006, the contents of which are incorporated herein by reference.

FIELD

The present invention relates to methods for remineralizing tooth surfaces of mammals, as well as methods of imparting acid resistance thereto. The methods employ chewing gum or confectionery compositions for delivery of casein phosphopeptide-calcium phosphate and a food-grade acid into the oral cavity of a mammal. The present invention also relates to chewing gum and confectionery compositions that remineralize and/or impart acid resistance to tooth surfaces of mammals.

BACKGROUND

The formation of dental caries in teeth has been well studied. Although the use of fluorides has decreased the prevalence of dental caries, the disease continues to remain a public health problem. Caries are understood to result from the accumulation of plaque on the teeth and the production of organic acids (plaque acids) when plaque microorganisms ferment sugars and starches in food. Before being washed away by saliva, the acids accumulate in the plaque long enough to lower the pH and to cause some of the enamel, a calcium-phosphorous mineral known as hydroxyapatite, to dissolve, that is, demineralize, which can lead to dental caries (tooth decay), and sensitivity.

Further, many chewing gum and confectionery products, particularly fruit-flavored products, contain acids, for example, as part of the flavor or taste system. Many consumers, especially children, enjoy fruit-flavored chewing gum and confectionery products. The acids, however, can cause demineralization of the tooth surface, which may lead to dental caries.

Efforts have been made over the years to address the problem of dissolution or demineralization of tooth enamel and the resultant formation of dental caries. Casein phosphopeptide-calcium phosphate complexes are known to have anti-cariogenic teeth strengthening effects when used as dentrifrices. The complexes, also known as CPP-ACP complexes or calcium casein peptone-calcium phosphate, are calcium phosphate stabilized by casein phosphopeptides. CPP-ACP counteracts demineralization by enhancing remineralization while buffering plaque acid. It acts by localizing calcium and phosphate ions in dental plaque at the tooth surface. This increased level of calcium and phosphate in dental plaque helps buffer plaque acid and maintain a state of supersaturation of calcium and phosphate in solution, i.e., in the saliva.

U.S. Pat. Nos. 5,130,123 and 5,227,154 teach casein phosphopeptides in prevention of dental caries. WO 98/40406 teaches phosphopeptide-calcium phosphate complexes to provide anti-caries efficacy. U.S. Pat. Nos. 6,846,500 and 6,733,818 disclose chewing gum and confectionery products containing a combination of casein phosphopeptide-amorphous calcium phosphate with sodium bicarbonate.

Dental caries, however, continues to be a problem in many communities. The high cost to individuals and the community in treating dental caries has necessitated the development of new caries-preventive products.

There is a need, therefore, for new methods of reducing dental caries. As many consumers enjoy chewing gum and confectionery products, there is a need for reducing dental caries employing such products, particularly sugarless products. Chewing gum and confectionery products that slow the progression of carious lesions, as well as enhance the regression thereof are needed. Further, there is a need for acid-containing chewing gum and confectionery compositions that can impart both remineralization and acid resistance to the tooth surfaces of mammals.

SUMMARY

In some embodiments there is a chewing gum composition including a gum base, at least one sweetening agent, casein phosphopeptide-calcium phosphate and at least one food-grade acid.

Some embodiments provide a confectionery composition including a confectionery carrier, at least one sweetening agent, casein phosphopeptide-calcium phosphate and at least one food-grade acid.

Some embodiments provide a method of remineralizing the tooth surface of a mammal, which includes: (a) applying a chewing gum product into the oral cavity of the mammal, wherein the chewing gum product contains a gum base, at least one sweetening agent, casein phosphopeptide-calcium phosphate and at least one food-grade acid; and (b) chewing the chewing gum product for a time sufficient to remineralize the tooth surface of the individual.

Some embodiments provide a method of imparting acid resistance to the tooth surface of a mammal, which includes: (a) applying a chewing gum product into the oral cavity of the mammal, wherein the chewing gum product includes a gum base, at least one sweetening agent, casein phosphopeptide-calcium phosphate and at least one food-grade acid; and (b) chewing the chewing gum product for a time sufficient to impart acid resistance to the tooth surface of the mammal.

In some embodiments there is a method of remineralizing the tooth surface of a mammal, which includes: (a) applying a confectionery product into the oral cavity of the mammal, wherein the confectionery product contains a confectionery carrier, at least one sweetening agent, casein phosphopeptide-calcium phosphate and at least one food-grade acid; and (b) retaining the confectionery product in the oral cavity for a time sufficient to remineralize the tooth surface of the individual.

In some embodiments there is a method of imparting acid resistance to the tooth surface of a mammal, which includes: (a) applying a confectionery product into the oral cavity of the mammal, wherein the confectionery product includes a confectionery carrier, at least one sweetening agent, casein phosphopeptide-calcium phosphate and at least one food-grade acid; and (b) retaining the confectionery product in the oral cavity for a time sufficient to impart acid resistance to the tooth surface of the mammal.

Some embodiments provide a kit for remineralizing the tooth surface of a mammal including: (a) a chewing gum product containing a gum base, casein phosphopeptide-calcium phosphate and at least one food-grade acid; (b) a set of instructions for using the chewing gum product; and (c) a package for housing the chewing gum product and the set of instructions.

Some embodiments provide a kit for remineralizing the tooth surface of a mammal including: (a) a confectionery product which includes a confectionery carrier, casein phosphopeptide-calcium phosphate and at least one food-grade acid; (b) a set of instructions for using the confectionery product; and (c) a package for housing the confectionery product and the set of instructions.

Some embodiments provide a kit for imparting acid resistance to the tooth surface of a mammal including: (a) a chewing gum product which includes a gum base, casein phosphopeptide-calcium phosphate and at least one food-grade acid; (b) a set of instructions for using the chewing gum product; and (c) a package for housing the chewing gum product and the set of instructions.

Some embodiments provide a kit for imparting acid resistance to the tooth surface of a mammal which includes: (a) a confectionery product including a confectionery carrier, casein phosphopeptide-calcium phosphate and at least one food-grade acid; (b) a set of instructions for using the confectionery product; and (c) a package for housing the confectionery product and the set of instructions.

DETAILED DESCRIPTION

Embodiments described herein provide chewing gum and confectionery products containing casein phosphopeptide-calcium phosphate (CPP-ACP), which is an anticaries agent, and methods of employing such compositions to improve the dental health of mammals.

Some embodiments described herein provide chewing gum or confectionery compositions, particularly sugarless compositions, for reducing dental caries in a mammal. The chewing gum or confectionery composition may include a gum base or confectionery carrier, respectively, at least one sweetening agent and CPP-ACP. High levels of CPP-ACP may be used in the compositions to reduce dental caries. CPP-ACP can also be used with other oral care actives as part of a multi-functional oral care product. These other oral care actives can include, but are not limited to whitening actives, antimicrobial actives, breath freshening actives, de-sensitizing actives, and other remineralizing actives. Methods of reducing dental caries also are described herein employing the chewing gum or confectionery compositions. Such methods may slow the progression and enhance the regression of carious lesions to a substantially greater extent than similar products that are free of CPP-ACP.

Some other embodiments described herein provide acid-containing chewing gum or confectionery compositions, particularly sugarless compositions, for remineralizing and/or imparting acid resistance to the tooth surface of a mammal. The chewing gum or confectionery composition may include a gum base or confectionery carrier, respectively, at least one sweetening agent, CPP-ACP and a food-grade acid. Methods of remineralizing and/or imparting acid resistance to the tooth surface of a mammal also are described herein employing the chewing gum and confectionery compositions.

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the terms "bubble gum" and "chewing gum" are used interchangeably and are both meant to include any gum compositions.

The term "food-grade acid," as used herein, encompasses any acid that is acceptable for use in edible compositions.

As used herein, the term "center-fill" refers to the innermost region of a center-fill gum or confectionery product. The term "center-fill" does not imply symmetry of a gum or confectionery product, only that the "center-fill" is within another region of the product. In some embodiments, more than one center-fill may be present.

As used herein, the term "gum region" or "confectionery region" refers to a region of a center-fill gum or confectionery product, respectively, that may be adjacent to or at least partially surrounding the center-fill, or innermost, region. In some embodiments, the gum region or confectionery region is an intermediate region.

As used herein, the terms "coating" or "coating region" are used to refer to the outermost region of a center-fill gum or confectionery product.

As used herein, the terms "surround," "surrounding," and the like are not limited to encircling. These terms may refer to enclosing or confining on all sides, encircling or enveloping, and are not limited to symmetrical or identical thicknesses for a region in a center-fill gum or confectionery product.

Compositions and Methods for Reducing Dental Caries

As mentioned above, embodiments described herein provide compositions and methods for reducing dental caries. The compositions may be chewing gum or confectionery compositions, which may include CPP-ACP, an anticaries agent. Such compositions may lead to significantly greater reductions in dental caries compared to similar compositions that are free of CPP-ACP.

The chewing gum compositions may include a gum base, at least one sweetening agent and CPP-ACP. Chewing gum compositions may be provided in a variety of different forms, such as, for example, slab, pellet, sticks, center-fill gums, deposited gums and compressed gums. The confectionery compositions may include a confectionery carrier, at least one sweetening agent and CPP-ACP. Confectionery compositions may be provided in a variety of different forms, such as, for example, hard candy, soft candy, cotton candy, pressed tablets, lozenges, nougats, caramels, frappes and taffies. The chewing gum and confectionery compositions also may include at least one flavor and a variety of optional additives.

As mentioned above, chewing gum compositions may include a gum base. The gum base may include any component known in the chewing gum art. Such components may be water soluble, water-insoluble or a combination thereof. For example, the gum base may include elastomers, bulking agents, waxes, elastomer solvents, emulsifiers, plasticizers, fillers and mixtures thereof.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight, desirably from about 35% to about 40% by weight.

In some embodiments, the gum base may include wax. It softens the polymeric elastomer mixture and improves the elasticity of the gum base. When present, the waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other ingredients, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include hydrogenated vegetable oils, such as soybean oil and cottonseed oils, which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

In some embodiments, the gum base may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional ingredients may be optionally included in the gum base in effective amounts such as flavor agents and coloring agents, antioxidants, preservatives, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, vitamin E and mixtures thereof, may also be included. Other conventional chewing gum additives known to one having ordinary skill in the chewing gum art may also be used in the gum base.

In general, the gum base is present in amounts of about 5% to about 95% by weight of the chewing gum composition. More specifically, the gum base may be present in amounts of about 20% to about 60% by weight of the chewing gum composition.

Chewing gum products may be prepared using standard techniques and equipment known to those skilled in the art. The apparatus useful in accordance with the embodiments described herein includes mixing and heating apparatus well known in the chewing gum manufacturing arts, and therefore the selection of the specific apparatus will be apparent to the artisan. For general chewing gum preparation processes see U.S. Pat. No. 4,271,197 to Hopkins et al, U.S. Pat. No. 4,352,822 to Cherukuri et al and U.S. Pat. No. 4,497,832 to Cherukuri et al, each of which is incorporated herein by reference in its entirety.

In compressed gum formats, the gum base may be in a particulate form, such as, but not limited to, a powdered or granular gum base, as opposed to molten or thermoplastic gum base. The particulate gum base may be essentially free of water and can readily be formed into any desired shape, such as by compression.

The particulate gum base may be formed using standard grinding techniques known in the art. The starting material may be any conventional gum base, such as those used to produce molten gum bases. The particulate gum base may be formed, for example, by shredding, grinding or crushing the gum base or other processes, as described in U.S. Pat. Nos. 3,262,784, 4,405,647, 4,753,805 and 6,290,985 and U.S. Publication No. 2003/00276871, all of which are incorporated herein by reference in their entirety.

Desirably, the particulate gum base is ground or the like into a particulate form that is similar in particle size to the tableting powder. By using components of like particle size, a homogenous mix of gum base and tableting powder may be achieved, which may provide a gum tablet of similar homogenous make-up. The gum base and tableting powder may have a particle size of about 4 to about 100 mesh, desirably about 8 to about 25 mesh, and more desirably about 12 to about 20 mesh.

The particulate gum base may be present in amounts of about 10% to about 80% by weight of the chewing gum composition, or tablet, desirably about 20% to about 50% by weight, and more desirably about 30% to. about 40% by weight.

The particulate gum base may be combined with a tableting powder to form the pressed gum tablet. The tableting powder can be in a dry, finely-divided form. Desirable particle size is provided above. The tableting powder may be a sucrose-based, dextrose-based or polyol-based powder, or combinations thereof. For example, the polyol-based powder may be a sorbitol or mannitol powder. The tableting powder may include other optional ingredients, such as flavor agents, color agents, sugar and/or sugarless sweeteners, and the like and combinations thereof.

In some embodiments, it may be desirable to combine a food-grade lubricant with the particulate gum base and tableting powder. Food-grade lubricants may assist in processing the gum composition into pressed tablets. More specifically, lubricants are used to prevent excess wear on dies and punches in tableting manufacture. Lubricants may be useful immediately after compression of the tablet within the die to reduce friction between the tablet and inner die wall.

The food-grade lubricant may be added separately or it may be included with the tableting powder, as in some commercially available tableting powders. Examples of suitable food-grade lubricants include: metallic stearates; fatty acids; hydrogenated vegetable oil; partially hydrogenated vegetable oils; animal fats; polyethylene glycols; polyoxyethylene monostearate; talc; silicon dioxide; and combinations thereof. Food-grade lubricants may be present in amounts of about 0-6% by weight of the gum composition.

Alternatively, in some embodiments, a compressible chewing gum composition can be formed by preparing a chewing gum composition and then grinding the mixture. The chewing gum composition can be prepared by mixing together molten gum base, bulk sweeteners, softeners, plasticizers, other sweeteners, colors, and the like by any known mixing technique such as dough mixing. As with preparation of the particulate gum base, the chewing gum mixture can be formed into a particulate chewing gum composition using standard grinding techniques known in the art. The particulate chewing gum may be formed, for example, by shredding, grinding or crushing the chewing gum or other processes, as described in U.S. Pat. Nos. 3,262,784, 4,405,647, 4,753,805 and 6,290, 985 and U.S. Publication No. 2003/00276871, all of which are incorporated herein by reference in their entirety.

As described above, the compressible chewing gum composition can be in the form of a pressed gum tablet. In some embodiments, the particulate gum base and modified release ingredients are pressed into a tablet form. Upon chewing, the pressed gum tablet consolidates into a soft chewy substance.

In some embodiments, the compressible chewing gum composition is a single-layer pressed tablet. In some embodiments, the compressible chewing gum composition is a multi-layer pressed tablet. Multi-layer tablet embodiments may have any desirable number of layers. Different layers may have the same or different thicknesses. In addition, different layers may include the same or different ingredients.

The pressed gum tablet also may have a coating layer surrounding the tablet. The coating layer may contain any ingredients conventionally used in the chewing gum art. For instance, the coating may contain sugar, polyols or high intensity sweeteners or the like, coloring agents, flavor agents and warming and/or cooling agents, among others.

The compressible chewing gum compositions, or pressed tablets, desirably have a very low moisture content. In some embodiments, the tablets are essentially free of water. Accordingly, some embodiments have a total water content of greater than about 0% to about 5% by weight of the composition. The density of the composition, or tablet, may be about 0.2 to about 0.8 g/cc. Further, the compressible chewing gum compositions, or tablets, may have a dissolution rate of about 1 to about 20 minutes. When in a pressed tablet form, the chewing gum may have a Shore hardness of about 30 to about 200.

In contrast to dough mixed chewing gums where the gum mixture can achieve temperatures of 35° C. to 60° C., compressed chewing gum temperatures can remain around ambient temperature (23° C. to 25° C.). In some embodiments, subjecting the compressible chewing gum compositions to lower temperatures can protect temperature sensitive ingredients from thermal degradation. Similarly, the absence of intimate mixing at temperatures above ambient can protect delivery systems that include temperature sensitive ingredients or ingredients subject to degradation from gum ingredients such as flavors, plasticizers, etc. Thus, ingredients susceptible to thermal or chemical degradation due to conventional dough mixing can be less likely to experience degradation in compressed chewing gum systems.

Confectionery compositions include confections other than chewing gum compositions. Instead of a gum base, confectionery compositions may include a confectionery carrier. The confectionery carrier may be selected from a variety of well-known carriers in the art. Selection of suitable carriers depends upon the type of confection being prepared.

In general a hard boiled candy confection has a base composed of a mixture of sugar or sugarless sweetening agents and other carbohydrate bulking agents kept in an amorphous or glassy condition. In some embodiments, the at least one sweetening agent itself may act as the carrier for the confectionery composition, or additional carrier components may be employed. Any of the sweetening agents set forth below may be used. A general discussion of the composition and preparation of hard confections may be found in E. B. Jackson, Ed. "Sugar Confectionery Manufacture", 2nd edition, Blackic Academic & Professional Press, Glasgow UK, (1990), at pages 129-169, as well as in H. A. Lieberman, Pharmaceutical Dosage Forms: Tablets, Volume 1 (1980), Marcel Dekker, Inc., New York, N.Y. at pages 339 to 469, which disclosure is incorporated herein by reference.

Such confectionery compositions may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavors, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavors, colorants and other additives during conventional manufacturing of hard confectionery is determined by the time needed to obtain a uniform distribution of the materials. Normally, mixing times of from 4 to 10 minutes have been found to be acceptable.

Once the candy mass has been properly tempered, it may be cut into workable portions or formed into desired shapes. A variety of forming techniques may be utilized depending upon the shape and size of the final product desired.

Soft candy confectionery compositions includes fondants, caramels toffees, fudge, marshmallows and nougats and the like and may also include jams and jellies. The preparation of soft confectionery compositions, such as nougat, involves conventional methods, such as the combination of two primary components, namely (1) a high boiling syrup, and (2) a relatively light textured frappe, generally prepared from egg albumin, gelatin, vegetable proteins, such as soy derived compounds, milk derived compounds such as milk proteins, and mixtures thereof. A general discussion of the composition and preparation of such confections may be found in E. B. Jackson. Ed. "Sugar Confectionery Manufacture", 2nd edition, Blackie Academic & Professional Press. Glasgow UK (1990), at pages 170-235.

The high boiling syrup, or "bob syrup", of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like may be added thereafter also under agitation. A general discussion of the composition and preparation of nougat confections may be found in B. W. Minifie, Chocolate, Cocoa and Confectionery: Science and Technology, 2nd edition, AVI Publishing Co., Inc., Westport, Conn. (1980), at pages 424-425, which disclosure is incorporated herein by reference.

The procedure for preparing the soft confectionery involves known procedures. In general, the frappe component is prepared first and thereafter the syrup component is slowing added under agitation at a temperature of at least about 65° C., and preferably at least about 100° C. The mixture of components is continued to be mixed to form a uniform mixture, after which the mixture is cooled to a temperature below 80° C., at which point, the flavor may be added. The mixture is further mixed for an additional period until it is ready to be removed and formed into suitable confectionery shapes.

Compressed tablet confectionery compositions contain particular materials and are formed into structures under pressure. These confections generally contain sugar or sugar substitutes in amounts up to about 95%, by weight of the composition, and typical tablet excipients such as binders and lubricants.

In general, the confectionery carrier is present in amounts of about 5% to about 99% by weight of the confectionery composition. More specifically, the confectionery carrier may be present in amounts of about 80% to about 99% by weight of the confectionery composition.

Both the chewing gum and confectionery compositions described herein may include at least one sweetening agent. Sweetening agents include sugars, sugarless bulk sweeteners, high intensity sweeteners, or the like, or mixtures thereof.

Suitable sugar sweeteners generally include mono-saccharides, di-saccharides and poly-saccharides such as but not limited to, sucrose (sugar), dextrose, maltose, dextrin, xylose, ribose, glucose, mannose, galactose, fructose (levulose), invert sugar, fructo oligo saccharide syrups, partially hydrolyzed starch, corn syrup solids and mixtures thereof.

Suitable sugarless bulk sweeteners include sugar alcohols (or polyols) such as, but not limited to, sorbitol, xylitol, mannitol, galactitol, maltitol, hydrogenated isomaltulose (ISOMALT), lactitol, erythritol, hydrogenated starch hydrolysates, and mixtures thereof.

Suitable hydrogenated starch hydrolysates include those disclosed in U.S. Pat. No. 4,279,931 and various hydrogenated glucose syrups and/or powders which contain sorbitol, maltitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN®, a commercially available product manufactured by Roquette Freres of France, and HYSTAR®, a commercially available product manufactured by SPI Polyols, Inc. of New Castle, Del., are also useful.

In some embodiments, high-intensity sweeteners may be used. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, xylitol, erythritol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame), N-[N-(3,3-dimethylbutyl)-L-α-aspartyl]-L-phenylalanine 1-methyl ester (Neotame), and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructofuranoside, or 4,1'-dichloro-4,1'-dideoxygalactosucrose; 1',6'-dichloro 1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro-4,6,1',6'-tetradeoxygalacto-sucrose; and 4,6,1',6'-tetradeoxy-sucrose, and mixtures thereof;

(e) protein based sweeteners such as thaumaoccous danielli (Thaumatin I and II) and talin;

(f) the sweetener monatin (2-hydroxy-2-(indol-3-ylmethyl)-4-aminoglutaric acid) and its derivatives; and (g) the sweetener Lo han guo (sometimes also referred to as "Lo han kuo").

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

In general, the at least one sweetening agent is present in amounts of about 0.001% to about 95% by weight of the chewing gum or confectionery composition. More specifically, bulk sweeteners (sugars and sugarless bulk sweeteners) may be present in amounts of about 5% to about 95% by weight of the chewing gum or confectionery compositions. In some embodiments, bulk sweeteners may be present in amounts of about 40% to about 90% by weight of the chewing gum or confectionery composition. Intense sweeteners may be present in amounts from about 0.001% to about 3%, by weight of the composition, depending upon the sweetener or combination of sweeteners used. The exact range of amounts for each type of sweetener may be selected by those skilled in the art.

In addition, the chewing gum and confectionery compositions include CPP-ACP. As mentioned above, CPP-ACP is an anticaries agent. In general, CPP-ACP may be present in amounts of about 0.5% to about 5% by weight of the chewing gum or confectionery composition. In some embodiments, high levels of CPP-ACP may be used to reduce dental caries, for example by about 16.9% over a chewing gum or confectionery that is free of CPP-ACP. For instance, CPP-ACP may be present in amounts of at least about 3% by weight of the chewing gum or confectionery composition.

In some embodiments described herein, the chewing gum or confectionery composition may include an anticaries agent, which consists essentially of CPP-ACP. In such embodiments, the anticaries agent may be present in amounts of about 0.5% to about 5% by weight of the chewing gum or confectionery composition. In some embodiments, the anticaries agent may be present in amounts of at least about 3% by weight of the chewing gum or confectionery composition. In some embodiments, other oral care actives may be included with CPP-ACP in the chewing gum or confectionery composition.

In some embodiments, CPP-ACP may be incorporated into the chewing gum or confectionery composition in a modified release form. For instance, CPP-ACP may be encapsulated to provide modified release characteristics to the component. In general, partially or completely encapsulating CPP-ACP with an encapsulating material may delay release of the ingredient during consumption of the chewing gum or confectionery composition, thereby delaying when the ingredient becomes available inside the consumer's mouth, throat, and/or stomach, available to react or mix with another ingredient, and/or available to provide some sensory experience and/or functional or therapeutic benefit. This can be particularly true when the ingredient is water soluble or at least partially water soluble.

In some embodiments, CPP-ACP may be used in its encapsulated and/or its unencapsulated (sometimes referred to as "free") forms. In center-fill gum or confectionery embodiments, for example, CPP-ACP may be incorporated into one or more regions of the center-fill product in its encapsulated and/or unencapsulated forms. For example, in a center-fill gum, encapsulated CPP-ACP may be included in the gum region and unencapsulated CPP-ACP may be included in the center-fill region. Alternatively, in some embodiments a combination of encapsulated CPP-ACP and unencapsulated CPP-ACP may be included in the same region of the product. The encapsulated and unencapsulated forms may be used in the same or different amounts.

Suitable encapsulating materials for CPP-ACP may include water insoluble polymers, co-polymers, or other materials capable of forming a strong matrix, solid coating, or film as a protective barrier with or for the ingredient. In some embodiments, the encapsulating material may completely surround, coat, cover, or enclose the CPP-ACP. In other embodiments, the encapsulating material may only partially surround, coat, cover, or enclose the CPP-ACP. Different encapsulating materials may provide different release rates or release profiles for the encapsulated CPP-ACP. In some embodiments, encapsulating material used in a delivery system may include one or more of the following: polyvinyl acetate, polyethylene, crosslinked polyvinyl pyrrolidone, polymethylmethacrylate, polylactidacid, polyhydroxylkanoates, ethylcellulose, polyvinyl acetatephthalate, polyethylene glycol esters, methacrylicacid-co-methylmethacrylate, ethylene-vinylacetate (EVA) copolymer, and the like, and combinations thereof.

A more detailed discussion of suitable encapsulating materials and techniques is provided in assignee's co-pending PCT Application No. PCT/US06/19761, which published as International Publication No. WO 2006/127618, which is incorporated by reference herein in its entirety.

The chewing gum and confectionery compositions also may include amounts of conventional additives selected from the group consisting of plasticizers, softeners, emulsifiers, waxes, fillers, bulking agents (carriers, extenders, bulk sweeteners), mineral adjuvants, flavor agents and coloring agents, physiological cooling agents, warming agents, tingling agents, antioxidants, acidulants, thickeners, medicaments, oral care actives, such as other remineralization agents, antimicrobials and tooth whitening agents, as described in assignee's co-pending U.S. patent application Ser. No. 10/901,511, filed on Jul. 29, 2004 and entitled "Tooth Whitening Compositions and Delivery Systems Therefor," which is incorporated herein by reference in its entirety, and the like, and mixtures thereof. Some of these additives may serve more than one purpose. For example, in sugarless gum compositions, a sweetener, such as maltitol or other sugar alcohol, may also function as a bulking agent.

In some embodiments, for instance, the chewing gum or confectionery composition may include at least one flavor (flavorant, flavoring or flavor agent). The at least one flavor may include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, watermelon, apricot, banana, melon, apricot, ume, cherry, raspberry, blackberry, tropical fruit, mango, mangosteen, pomegranate, papaya and so forth. Other potential flavors whose release profiles can be managed include a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with the cooling agents, described herein below.

In some embodiments, other flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference. These may include natural as well as synthetic flavors.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, .e., melonal (melon), 2,6-dimethyloctanal (green fruit), and 2-dodecenal (citrus, mandarin), cherry, grape, blueberry, blackberry, strawberry shortcake, and mixtures thereof.

In some embodiments, a flavoring agent may be employed in either liquid form and/or dried form. When employed in the latter form, suitable drying means such as spray drying the liquid may be used. Alternatively, the flavoring agent may be absorbed onto water soluble materials, such as cellulose, starch, sugar, maltodextrin, gum arabic and so forth or may be encapsulated. In still other embodiments, the flavoring agent may be adsorbed onto silicas, zeolites, and the like.

In some embodiments, the flavoring agents may be used in many distinct physical forms. Without being limited thereto, such physical forms include free forms, such as spray dried, powdered, beaded forms, encapsulated forms, and mixtures thereof.

In general, the at least one flavor is present in amounts of about 0.1% to about 15% by weight of the chewing gum or confectionery composition. More specifically, flavors may be present in amounts of about 0.5% to about 5.0% by weight of the chewing gum or confectionery compositions.

Coloring agents may be used in amounts effective to produce the desired color. The coloring agents may include pigments which may be incorporated in amounts up to about 6%, by weight of the chewing gum or confectionery composition. For example, titanium dioxide may be incorporated in amounts up to about 2%, and preferably less than about 1%, by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No.2, which is the disodium salt of 5,5-indigotindisulfonic acid. Similarly, the dye known as F.D.& C. Green No.1 comprises a triphenylmethane dye and is the monosodium salt of 4-[4-(N-ethyl-p-sulfoniumbenzylamino)diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

A variety of well-known cooling agents may be employed. For example, among the useful cooling agents are included menthol, xylitol, erythritol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol and glutarate esters, among others, and combinations thereof. These and other suitable cooling agents are further described in the following U.S. patents, all of which are incorporated in their entirety by reference hereto: U.S. Pat. Nos. 4,230,688 and 4,032,661 to Rowsell et al.; U.S. Pat. No. 4,459,425 to Amano et al.; U.S. Pat. No. 4,136,163 to Watson et al.; and U.S. Pat. No. 5,266,592 to Grub et al.

Warming agents may be selected from a wide variety of compounds known to provide the sensory signal of warming to the individual user. These compounds offer the perceived sensation of warmth, particularly in the oral cavity, and often enhance the perception of flavors, sweeteners and other organoleptic components. Useful warming agents include those having at least one allyl vinyl component, which may bind to oral receptors. Examples of suitable warming agents include, but are not limited to: vanillyl alcohol n-butylether (TK-1000, supplied by Takasago Perfumery Company Ltd., Tokyo, Japan); vanillyl alcohol n-propylether; vanillyl alcohol isopropylether; vanillyl alcohol isobutylether; vanillyl alcohol n-aminoether; vanillyl alcohol isoamylether; vanillyl alcohol n-hexylether; vanillyl alcohol methylether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amylalcohol; benzyl alcohol; glycerine; chloroform; eugenol; cinnamon oil; cinnamic aldehyde; phosphate derivatives thereof; and combinations thereof.

Tingling agents may be employed to provide a tingling, stinging or numbing sensation to the user. Tingling agents include, but are not limited to: Jambu Oleoresin or para cress (*Spilanthes* sp.), in which the active ingredient is Spilanthol; Japanese pepper extract (*Zanthoxylum peperitum*), including the ingredients known as Saanshool-I, Saanshool-II and Sanshoamide; black pepper extract (*piper nigrum*), including the active ingredients chavicine and piperine; Echinacea extract; Northern Prickly Ash extract; red pepper oleoresin; and effervescing agents, such as edible acids and bases, which may be encapsulated. Tingling agents are described in U.S. Pat. No. 6,780,443 to Nakatsu et al., U.S. Pat. No. 5,407,665 to McLaughlin et al., U.S. Pat. No. 6,159,509 to Johnson et al. and U.S. Pat. No. 5,545,424 to Nakatsu et al., each of which is incorporated by reference herein in its entirety.

Other conventional gum or confectionery additives known to one having ordinary skill in the chewing gum or confectionery art also may be used in the compositions.

In some embodiments, the chewing gum or confectionery composition may be free of sodium bicarbonate. More specifically, some known chewing gums and confections have included sodium bicarbonate with CPP-ACP to reduce plaque upon consumption. Sodium bicarbonate also may be used as a filler. Embodiments described herein, however, may be free of sodium bicarbonate, and the CPP-ACP alone may reduce dental caries. In particular, CPP-ACP in amounts of at least about 3% by weight of the chewing gum or confectionery composition may reduce caries by about 16.9% over chewing gum and confectionery compositions that are free of CPP-ACP. Similarly, some embodiments described herein may be free of any mineral fillers.

Some embodiments are directed to chewing gum or confectionery compositions that consist essentially of some of the components described above. More specifically, in some embodiments, a chewing gum composition for reducing dental caries may consist essentially of a gum base, at least one sweetening agent, CPP-ACP present in amounts of at least about 3% by weight of the chewing gum composition, at least one flavor, at least one coloring agent and at least one surfactant. Similarly, in some embodiments, a confectionery composition may consist essentially of a confectionery carrier, at least one sweetening agent, CPP-ACP present in amounts of at least about 3% by weight of the confectionery composition, at least one flavor and at least one coloring agent.

As mentioned above, the chewing gum compositions may be provided as a variety of different products, such as, slab, pellet, sticks, center-fill gums, deposited gums and compressed gums. The confectionery compositions also may be provided as a variety of different products, such as, hard candy, soft candy, center-fill candy, cotton candy, pressed tablets, lozenges, edible films, nougats, caramels, frappes and taffies. Any of the chewing gum or confectionery products may have a coating thereon, which may at least partially surround or enrobe the product.

More specifically, in some embodiments, the chewing gum or confectionery product may include a chewing gum or confectionery region and a coating region. The chewing gum region may be formed from any of the chewing gum compositions described above. Similarly, the confectionery region may be formed from any of the confectionery compositions described above. The coating region may at least partially surround the chewing gum or confectionery region. CPP-ACP may be located in the chewing gum or confectionery region, in the coating region or in both regions.

Some other embodiments are directed to center-fill chewing gum or confectionery products. Center-fill chewing gums may include a center-fill region and a gum region at least partially surrounding or positioned adjacent to the center-fill region. The gum region may be formed from any of the chewing gum compositions described above. Center-fill confectioneries, such as, for example, center-fill candy, may include a center-fill region and a confectionery region, such as a hard or chewy candy region, at least partially surrounding or positioned adjacent to the center-fill region. The confectionery region may be formed from any of the confectionery compositions described above. CPP-ACP may be located in the gum or confectionery region, the center-fill region or in both regions.

The center-fill region of the gum or confectionery product may be a liquid, solid or semi-solid, gas, or the like. Embodiments that include a liquid center-fill composition, as well as some semi-solid center-fill compositions, may involve concerns regarding retention of the liquid center during manufacturing and shelf-life, as mentioned above. In chewing gum embodiments, it may be desirable, therefore, to employ gum region compositions with liquid-fill gums that substantially reduce or prevent leaking of the liquid center. Suitable gum region compositions are discussed in assignee's co-pending U.S. application Ser. No. 11/210,954, which is incorporated by referenced herein in its entirety.

In some embodiments, center-fill products also may include a coating region, which at least partially surrounds the gum or confectionery region.

In coated chewing gum and confectionery embodiments, the outer coating may be soft, hard or crunchy. Any suitable coating materials known to those skilled in the art may be employed. Typically, the outer coating may include sorbitol, maltitol, xylitol, isomalt, erythritol and other crystallizable polyols; sucrose may also be used. Furthermore the coating may include several opaque layers, such that the chewing gum or confectionery composition is not visible through the coating itself, which can optionally be covered with a further one or more transparent layers for aesthetic, textural and protective purposes. The outer coating may also contain small amounts of water and gum arabic. The coating can be further coated with wax. The coating may be applied in a conventional manner by successive applications of a coating solution, with drying in between each coat. As the coating dries it usually becomes opaque and is usually white, though other colorants may be added. A polyol coating can be further coated with wax. The coating can further include colored flakes or speckles. If the composition includes a coating, it is possible that one or more oral care actives can be dispersed throughout the coating. This is especially preferred if one or more oral care actives is incompatible in a single phase composition with another of the actives. Flavors may also be added to yield unique product characteristics.

Other materials may be added to the coating to achieve desired properties. These materials may include without limitations, cellulosics such as carboxymethyl cellulose, gelatin, xanthan gum and gum arabic.

The coating composition may be applied by any method known in the art including the method described above. The coating composition may be present in an amount from about 2% to about 60%, more specifically from about 25% to about 45% by weight of the total chewing gum or confectionery product.

Center-fill products may be formed by any technique known in the art, which includes the method described by U.S. Pat. No. 6,280,780 to Degady et al. ("Degady"), which is incorporated by reference herein in its entirety.

Some embodiments described herein extend to methods of reducing or preventing dental caries in mammals, particularly by slowing the progression and enhancing the regression of carious lesions. Such methods may be particularly useful for reducing or preventing dental caries in humans. In accordance therewith, any of the chewing gum or confectionery products described above may be applied into the oral cavity of a mammal. The product may include a gum base, for chewing gums, or a confectionery carrier, for confectioneries, at least one sweetening agent and CPP-ACP, as described herein. Any of the other optional additives described above also may be included.

Once the chewing gum product is applied into the oral cavity, it may be chewed for a time sufficient to reduce caries formation. Similarly, once the confectionery product is applied into the oral cavity, it may be retained therein for a time sufficient to reduce caries formation. More specifically, in some embodiments, such time periods may be sufficient to slow the progression and enhance the regression of carious lesions. Such time periods may be at least 1 minute, more specifically, at least 10 minutes in some embodiments.

These methods may reduce or prevent caries formation to a greater extent than chewing a sugarless chewing gum product which is free of CPP-ACP for the same period of time. More specifically, chewing one of the chewing gum products described herein may reduce caries formation by about 16.9% over chewing sugarless chewing gum products which are free of CPP-ACP. Similarly, retaining one of the confectionery products described herein in the oral cavity may reduce caries formation by about 16.9% over confectioneries which are free of CPP-ACP.

Further, in some embodiments, the chewing gum or confectionery product may display a brand or logo (e.g., slogans, trademarks, terms and colors) that communicates the presence of CPP-ACP in an amount sufficient to reduce or prevent dental caries. In some embodiments, the chewing gum or confectionery product itself may display the brand or logo. In some other embodiments, the chewing gum or confectionery product may be housed within packaging that displays the brand or logo.

The brand or logo that communicates the presence of CPP-ACP further may be marketed to consumers in a variety of manners. Suitable marketing strategies, include, for example, print, radio, satellite radio, television, movie theater and online advertising campaigns, point-of-purchase advertisements, billboard advertisements, public transportation and telephone booth advertisements, instant messaging, ringtones, and the like.

Some embodiments described herein may extend to kits for addressing the problem of dental caries in mammals. In particular, in some embodiments, a kit may be provided for reducing dental caries in a mammal. The kit may include any of the chewing gum or confectionery products described herein. The kit also may include a set of instructions for using the chewing gum or confectionery product and a package for housing the chewing gum or confectionery product and the set of instructions. Similar kits for preventing dental caries in a mammal or for slowing the progression and enhancing the regression of carious lesions in a mammal also may be provided.

Compositions and Methods for Remineralizing and/or Imparting Acid Resistance to Tooth Surfaces As mentioned above, many consumers, particularly children, enjoy acid-containing chewing gums and confections. Acids may be used in chewing gums and confections for a variety of reasons. Sometimes acids are used to add flavor, such as in fruit-flavored gums, to add sourness, or to promote mouth-moistening, or the like. As mentioned above, however, acid-containing gums can lead to demineralization of the tooth surfaces.

Accordingly, some embodiments described herein extend to acid-containing compositions for remineralizing and/or imparting acid resistance to the tooth surface of a mammal. In general, these compositions may be chewing gum or confectionery products employing CPP-ACP in combination with a food-grade acid. Such products may remineralize and/or impart a greater degree of acid resistance to tooth surfaces than similar compositions that are free of CPP-ACP.

The chewing gum compositions may include a gum base, at least one sweetening agent, CPP-ACP and at least one food-grade acid. The chewing gum compositions may be provided in any of the forms described above.

The confectionery compositions may include a confectionery carrier, at least one sugarless sweetening agent, CPP-ACP and at least one food-grade acid. The confectionery compositions also may be provided in any of the forms described above.

The chewing gum or confectionery compositions also may include additional oral care actives, such as but not limited to, whitening actives, antimicrobial actives, breath freshening actives, de-sensitizing actives, and other remineralizing actives.

The chewing gum and confectionery compositions also may include at least one flavor and a variety of optional additives. Sugarless compositions may be desirable and include sugarless sweetening agents, as set forth above.

The gum base, confectionery carrier, sweetening agents, flavors and optional additives, such as coloring agents, employed in the chewing gum and confectionery compositions all are described above in the section entitled "Compositions and Methods for Reducing Dental Caries." These components may be used in the same amounts described above.

The chewing gum and confectionery compositions also include CPP-ACP and at least one food-grade acid. As described above, CPP-ACP generally may be present in amounts of about 0.5% to about 5% by weight of the chewing gum or confectionery composition. More specifically, in some chewing gum and confectionery embodiments for remineralizing and/or imparting acid resistance to tooth surfaces, CPP-ACP may be present in amounts of about 0.5% to about 1.5% by weight of the composition.

The at least one food-grade acid included in the chewing gum and confectionery compositions may include, but is not limited to: acetic acid; adipic acid; ascorbic acid; butyric acid; citric acid; formic acid; fumaric acid; glyconic acid; lactic acid; malic acid; phosphoric acid; oxalic acid; succinic acid; tartaric acid; and combinations thereof.

Food-grade acids may be present in amounts of about 0.01% to about 20% by weight of the chewing gum or confectionery composition. More specifically, in some embodiments, food-grade acids may be present in amounts of about 0.5% to about 5% by weight of the chewing gum or confectionery composition, and even more specifically about 2.5% to about 5% by weight of the chewing gum or confectionery composition.

The chewing gum and confectionery compositions may include any of the other additives described above. In addition, the chewing gum and confectionery compositions may be provided in any of the product forms discussed above, such as, for example, center-fill gums and confectioneries. Moreover, as described above, the CPP-ACP may be present in a variety of different regions of the product in some embodiments.

Also as discussed above, the CPP-ACP may be used in its encapsulated and/or unencapsulated form. The at least one food-grade acid also may be used in its encapsulated and/or unencapsulated form. The CPP-ACP and food-grade acid may be encapsulated separately or together as a mixture. In some embodiments in which the CPP-ACP and food-grade acid are separately encapsulated, the same or different encapsulating materials may be used.

In center-fill gum or center-fill confectionery embodiments, for example, CPP-ACP and at least one food-grade acid may be incorporated into one or more regions of the center-fill product in their encapsulated and/or unencapsulated forms. For example, in a center-fill gum, encapsulated CPP-ACP may be included in the gum region and an encapsulated food-grade acid may be included in the center-fill region. Alternatively, a mixture of CPP-ACP and a food-grade acid may be encapsulated together and incorporated into one or more regions of the product. In some other embodiments, at least one of the components may be used in its encapsulated and unencapsulated forms. For example, CPP-ACP may be included in its encapsulated and unencapsulated forms in combination with a food-grade acid, which may or may not be encapsulated. The encapsulated and unencapsulated forms may be used in the same or different amounts.

In some embodiments, the chewing gum or confectionery product also may display a brand or logo, or be housed within packaging that displays a brand or logo, as described above.

Some embodiments described herein extend to methods of remineralizing tooth surfaces of mammals, as well as methods of imparting acid resistance to tooth surfaces of mammals. Such methods may be particularly useful for remineralizing and/or imparting acid resistance to tooth surfaces of humans. In accordance with such methods, any of the chewing gum or confectionery products described above may be applied into the oral cavity of a mammal. The product may include a gum base, for chewing gums, or a confectionery carrier, for confectioneries, at least one sweetening agent, CPP-ACP and at least one food-grade acid, as described herein. Any of the other optional additives described above also may be included.

Once the chewing gum product is applied into the oral cavity, it may be chewed for a time sufficient to remineralize the tooth surface of the mammal. Similarly, once the confectionery product is applied into the oral cavity, it may be retained therein for a time sufficient to reduce caries formation. Such time periods may be at least 1 minute, more specifically, at least 10 minutes in some embodiments.

These methods may remineralize tooth surfaces to a greater extent than chewing a chewing gum product which is free of CPP-ACP for the same period of time. More specifically, chewing one of the chewing gum products described above may lead to at least about 10% more remineralization than chewing gums which include a food-grade acid, but are free of CPP-ACP. In addition, chewing one of the chewing gums described above may cause at least 3% more remineralization than chewing gums which are free of both CPP-ACP and food-grade acid. The same remineralization benefits may be achieved with the confectionery products described above. These benefits may be particularly applicable in sugarless gums and confectionery products.

In accordance with some embodiments, chewing one of the chewing gums or confectioneries described above may impart a greater amount of acid resistance to tooth surfaces than a chewing gum product which is free of CPP-ACP for the same period of time. More specifically, the chewing gum products described above may impart at least about 13% more acid resistance than chewing gums which include a food-grade acid, but are free of CPP-ACP. Additionally, the chewing gums described above may impart at least 4% more acid resistance than chewing gums which are free of both CPP-ACP and food-grade acid. The same acid resistance benefits may be achieved with the confectionery products described above. These benefits also may be particularly applicable in sugarless gums and confectionery products.

Some embodiments described herein may extend to kits for addressing the problem of demineralization of tooth surfaces in mammals. In particular, in some embodiments, a kit may be provided for remineralizing tooth surfaces. The kit may include any of the chewing gum or confectionery products described above, which may include CPP-ACP and food-grade acid(s). The kit also may include a set of instructions for using the chewing gum or confectionery product and a package for housing the chewing gum or confectionery product and the set of instructions. Similar kits for imparting acid resistance to tooth surfaces in a mammal also may be provided.

The features and advantages of the present invention are more fully shown by the following examples which are provided for purposes of illustration, and are not to be construed as limiting the invention in any way.

EXAMPLES

Example 1

This example shows the anticariogenicity of sugarless chewing gum containing CPP-ACP as compared to that of a control sugarless chewing gum in a sample of adolescents employing usual oral hygiene practices.

A sugarless chewing gum slab containing CPP-ACP was prepared according to the formulation in Table 1 below. A control sugarless chewing gum slab, which is free of CPP-ACP, was prepared according to the formulation in Table 2 below.

TABLE 1

Sugarless Chewing Gum Slab Containing CPP-ACP

| Component | Weight % |
|---|---|
| Gum base | 32 |
| Softeners | 13.03 |
| Polyols - powdered | 48.345 |
| CPP-ACP | 3 |
| Coloring agent | 0.17 |
| Flavors | 1.85 |
| Menthol | 0.17 |
| Aspartame | 0.09 |
| Ace-K | 0.225 |
| Encapsulated Ace-K | 0.95 |
| Spray dried flavor enhancer | 0.17 |

TABLE 2

Sugarless Chewing Gum Slab Free of CPP-ACP ("control gum")

| Component | Weight % |
|---|---|
| Gum base | 32 |
| Softeners | 13.03 |
| Polyols - powdered | 51.345 |
| Coloring agent | 0.17 |
| Flavors | 1.85 |
| Menthol | 0.17 |
| Aspartame | 0.09 |
| Ace-K | 0.225 |
| Encapsulated Ace-K | 0.95 |
| Spray dried flavor enhancer | 0.17 |

Individual chewing gum pieces were formulated according to Table 1 above, containing 54.4 mg of CPP-ACP. The control gum was identical to the sugarless chewing gum containing CPP-ACP except formulated without the CPP-ACP.

The sugarless chewing gum containing CPP-ACP and the control gum were used in a two-year double-blind, randomized trial designed to measure the comparative reduction in dental caries. The trial was conducted using 2,720 adolescents (aged approximately 12 years) who were subjected to usual oral care hygiene over the two-year period, including normal dental visits and fluoride-containing drinking water. The gums were chewed three times a day for 10 minutes per session. The test group chewed the sugarless gum containing CPP-ACP and the control group chewed the control gum. Standardized digital radiographs (bitewing radiographs) of each subject's teeth were taken at the baseline and at the completion of the study (24 months) using the Dexis digital X-ray system. The radiographs were scored and assessed for approximal surface dental caries at both the enamel and dentine level. Analysis of caries progression or regression was undertaken using a transition matrix. The results evidenced a statistically significant difference in the distributions of the transition scores between the two groups.

In particular, the sugarless gum containing CPP-ACP slowed the progression of carious lesion as compared with the control gum. For subjects chewing the sugarless gum containing CPP-ACP, 814 (4.41%) of approximal surfaces experienced caries progression compared to 932 (5.31%) approximal surfaces in the control group, which is a reduction of 16.9% as compared to the control group. The trial also showed that the sugarless gum containing CPP-ACP enhanced regression of carious lesions compared to the control gum. In particular, 56 (0.30%) of approximal surfaces experienced caries regression with the sugarless gum containing CPP-ACP compared to 36 (0.21%) approximal surfaces with the control gum. Additionally, a greater percentage of approximal surfaces remained unchanged with the sugarless gum containing CPP-ACP than with the control gum. These results are provided in more detail in Table 3 below.

TABLE 3

Digital Radiograph Results

| Transition Score | Control Gum | CPP-ACP Gum | Difference in Percentages |
|---|---|---|---|
| −3 | 0 (0.00%) | 1 (0.01%) | 0.01 |
| −2 | 7 (0.04%) | 9 (0.05%) | 0.01 |
| −1 | 29 (0.17%) | 45 (0.24%) | 0.07 |
| 0 | 16573 (94.48%) | 17590 (95.29%) | 0.81 |
| 1 | 586 (3.34%) | 485 (2.63%) | −0.71 |
| 2 | 284 (1.62%) | 260 (1.41%) | −0.21 |
| 3 | 40 (0.23%) | 56 (0.30%) | 0.08 |
| 4 | 22 (0.13%) | 13 (0.07%) | −0.05 |
| All | 17541 (100.00%) | 18459 (100.00%) | |

In particular, the transition scores represent the transition from the baseline measurement to the measurement at the completion of the trial. Negative transition scores represent regression of dental caries, whereas positive transition scores represent progression of dental caries. As can be seen from Table 4, for example, the control gum resulted in 0.21% regression of dental caries, whereas the CPP-ACP containing gum resulted in 0.3% regression of dental caries, as mentioned above.

Therefore, the sugarless chewing gum containing 54.4 mg (3% by weight) of CPP-ACP significantly slowed progression and enhanced regression of dental caries in a two-year trial relative to a normal sugarless chewing gum.

Example 2

This example shows the remineralization and acid resistance effects of sugarless chewing gum containing CPP-ACP and a food-grade acid as compared to that of control sugarless chewing gums.

A sugarless chewing gum pellet containing CPP-ACP and citric acid was prepared according to the first formulation in Table 4 below. Two control sugarless chewing gum pellets were also prepared. The first control gum contained citric acid, but was free of CPP-ACP, as indicated by the second formulation in Table 4 below ("Control with acid"). The second control gum was free of both citric acid and CPP-ACP, as indicated by the third formulation in Table 4 below ("Control without acid").

TABLE 4

Chewing gum formulations

| Component | Weight % | | |
|---|---|---|---|
| | CPP-ACP and Acid | Control with acid | Control without acid |
| Maltitol | 43.963 | 44.733 | 45.462 |
| Gum base | 25.327 | 25.327 | 25.327 |

TABLE 4-continued

Chewing gum formulations

| Component | Weight % | | |
|---|---|---|---|
| | CPP-ACP and Acid | Control with acid | Control without acid |
| Xylitol | 22.134 | 22.134 | 22.134 |
| Flavors | 2.58 | 2.58 | 2.506 |
| Gum Arabic | 1.676 | 1.676 | 1.676 |
| Hydrogenated starch hydrolysate | 1.038 | 1.038 | 1.038 |
| Mannitol | 0.83 | 0.83 | 0.83 |
| CPP-ACP | 0.769 | 0 | 0 |
| Acid | 0.655 | 0.655 | 0 |
| Aspartame | 0.415 | 0.415 | 0.415 |
| Lecithin | 0.404 | 0.404 | 0.404 |
| Ace-K | 0.1 | 0.1 | 0.1 |
| Vegetable wax | 0.057 | 0.057 | 0.057 |
| Colors | 0.051 | 0.051 | 0.051 |

Individual chewing gum pellets were formulated according to each of the formulations in Table 4 above. The sugarless gum of the first formulation (2 pellets) contained 18.8 mg of CPP-ACP and 20 mg citric acid. The sugarless gum of the second formulation (2 pellets) contained 20 mg citric acid alone. The sugarless gum of the third formulation (2 pellets) contained no CPP-ACP or citric acid.

The three different sugarless chewing gums were used in a 14-day double-blind, randomized test designed to measure the remineralization and acid resistance effects of a CPP-ACP and acid-containing gum. The test was conducted using 10 subjects wearing removable palatal appliances. The palatal appliances each had 4 half-slab insets of human enamel containing demineralized subsurface lesions. The gums (2 pellets) were chewed 4 times a day for 20 minutes per session. At the end of each chewing session, the enamel half-slabs were removed and half of the remineralized lesion was treated with carbopol/lactic acid for 16 hours. The enamel slabs subsequently were embedded, sectioned and subjected to microradiography to determine the level of remineralization.

The remineralization and acid resistance results are shown in Table 5 below.

TABLE 5

| Results | | |
|---|---|---|
| Chewing gum | Remineralization | Acid resistance |
| CPP-ACP and Acid | 13.02 ± 2.23 | 2.18 ± 2.35 |
| Control with acid | 2.60 ± 1.30 | −11.48 ± 1.64 |
| Control without acid | 9.39 ± 1.17 | −2.82 ± 1.91 |

As can be seen from the results in Table 5, chewing the gum containing CPP-ACP and citric acid resulted in significantly higher remineralization than chewing either the gum containing no CPP-ACP or citric acid or the gum containing citric acid alone. In addition, the 16 hour acid resistance test of the remineralized lesions showed that the level of mineral after the acid test was significantly greater for the gum containing CPP-ACP and citric acid as compared with the two control gums.

Therefore, sugarless chewing gum containing CPP-ACP and acid significantly promoted remineralization of tooth surfaces.

Examples 3-6

The following are examples of modified release, i.e., encapsulated, forms of CPP-ACP and several food-grade acids (adipic, citric and malic). The encapsulated CPP-ACP of Example 3 may be used in chewing gum or confectionery compositions for reducing dental caries. The encapsulated CPP-ACP also may be used in combination with one or more of the encapsulated acids of Examples 4-6 to provide chewing gum or confectionery compositions for remineralizing and/or imparting acid resistance to tooth surfaces.

Moreover, each of the encapsulated components of Examples 3-6 may be incorporated into chewing gum or confectionery compositions in combination with the unencapsulated form of the component. For instance, the CPP-ACP of Example 3 may be combined with unencapsulated CPP-ACP for use in chewing gum or confectionery compositions for reducing dental caries. The encapsulated and unencapsulated forms may be used in the same or different amounts.

Similarly, each of the encapsulated acids of Examples 4-6 may be combined with free amounts of the same acid for use in chewing gum or confectionery compositions for remineralizing and/or imparting acid resistance to tooth surfaces. Combinations of different acids also may be used. The encapsulated and unencapsulated forms may be used in the same or different amounts.

EXAMPLE 3

| Encapsulation of CPP-ACP - Polyvinyl acetate matrix | |
|---|---|
| Composition: Ingredient | Weight percent |
| Polyvinyl Acetate | 55.00% |
| Hydrogenated Oil | 3.75% |
| Glycerol Monostearate | 1.25% |
| CPP-ACP | 40.00% |
| Total | 100.00% |

Polyvinyl acetate is melted at a temperature of about 80° C. in a high shear mixer such as extruder (single or twin screw) or sigma or Banbury mixer. The hydrogenated oil and glycerol monostearate are then added to the molten polyvinyl acetate. CPP-ACP is then added to the resulting mixture and mixed under high shear to completely disperse the ingredients. The resulting filled polymer melt is cooled and ground to produce a powdered material with a particle size of less than 420 microns. The encapsulated matrix is stored in air tight containers with low humidity below 35° C.

EXAMPLE 4

| Encapsulation of Adipic acid - Polyvinyl acetate matrix | |
|---|---|
| Composition: Ingredient | Weight percent |
| Polyvinyl Acetate | 60.00% |
| Hydrogenated Oil | 3.75% |
| Glycerol Monostearate | 1.25% |
| Adipic acid | 35.00% |
| Total | 100.00% |

Polyvinyl acetate is melted at a temperature of about 110° C. in a high shear mixer such as extruder (single or twin screw) or sigma or Banbury mixer. The hydrogenated oil and glycerol monostearate are then added to the molten polyvinyl acetate. Adipic acid is then added to the resulting mixture and mixed under high shear to completely disperse the ingredients. The resulting filled polymer melt is cooled and ground to produce a powdered material with a particle size of less than 420 microns. The encapsulated adipic acid matrix is stored in air tight containers with low humidity below 35° C.

EXAMPLE 5

Encapsulation of Citric Acid - Polyvinyl acetate matrix

| Composition: Ingredient | Weight percent |
|---|---|
| Polyvinyl Acetate | 55.00% |
| Hydrogenated Oil | 3.75% |
| Glycerol Monostearate | 1.25% |
| Citric Acid | 40.00% |
| Total | 100.00% |

Polyvinyl acetate is melted at a temperature of about 110° C. in a high shear mixer such as extruder (single or twin screw) or sigma or Banbury mixer. The hydrogenated oil and glycerol monostearate are then added to the molten polyvinyl acetate. Citric acid is then added to the resulting mixture and mixed under high shear to completely disperse the ingredients. The resulting filled polymer melt is cooled and ground to produce a powdered material with a particle size of less than 420 microns. The encapsulated citric acid matrix is stored in air tight containers with low humidity below 35° C.

EXAMPLE 6

Encapsulation of Malic acid - Polyvinyl acetate.

| Composition: Ingredient | Weight percent |
|---|---|
| Polyvinyl Acetate | 55.00% |
| Hydrogenated Oil | 3.75% |
| Glycerol Monostearate | 1.25% |
| Malic acid | 40.00% |
| Total | 100.00% |

Polyvinyl acetate is melted at a temperature of about 110° C. in a high shear mixer such as extruder (single or twin screw) or sigma or Banbury mixer. The hydrogenated oil and glycerol monostearate are then added to the molten polyvinyl acetate. Malic acid are then added to the resulting mixture and mixed under high shear to completely disperse the ingredients. The resulting filled polymer melt is cooled and ground to produce a powdered material with a particle size of less than 420 microns. The malic acid encapsulation matrix is stored in air tight containers with low humidity below 35° C.

The invention claimed is:

1. A chewing gum composition comprising:
   (a) a gum base;
   (b) at least one non-sugar sweetening agent;
   (c) casein phosphopeptide-calcium phosphate in an amount of about 0.5% to about 1.5% by weight of the composition; and
   (d) at least one food-grade acid comprising citric acid in an amount of from about 0.5 to about 2.5% by weight of the composition;
   wherein said composition provides remineralization of enamel in an amount that is at least about 10% greater than the amount provided by a sweetening agent containing chewing gum composition which comprises an equivalent amount of food-grade acid but which is free of casein phosphopeptide-calcium phosphate; and
   wherein said composition provides acid resistance to teeth in an amount that is at least about 4% greater than the amount provided by a sweetening agent containing chewing gum composition which comprises an equivalent amount of food-grade acid but which is free of casein phosphopeptide-calcium phosphate.

2. The chewing gum composition of claim 1, wherein said gum base is present in amounts of about 5% to about 95% by weight of said composition.

3. The chewing gum composition of claim 1, wherein said at least one sweetening agent is present in amounts of about 0.001% to about 95% by weight of said composition.

4. The chewing gum composition of claim 1, wherein said casein phosphopeptide-calcium phosphate is present in amounts of about 0.5% to about 0.769% by weight of said composition.

5. The chewing gum composition of claim 1, wherein said food-grade acid is present in amounts of about 0.5% to about 0.655% by weight of said composition.

6. The chewing gum composition of claim 1, wherein said non-sugar sweetening agent is selected from the group consisting of sugarless bulk sweeteners, high-intensity sweeteners and combinations thereof.

7. The chewing gum composition of claim 1, further comprising at least one flavor.

8. The chewing gum composition of claim 1, wherein said chewing gum composition comprises a chewing gum product selected from the group consisting of slab, pellet, stick, center-fill gum, deposited gum and compressed gum.

9. The chewing gum composition of claim 8, wherein said chewing gum product comprises a chewing gum region and a coating region and said casein phosphopeptide-calcium phosphate is located in a region selected from the group consisting of said chewing gum region, said coating region and combinations thereof.

10. The chewing gum composition of claim 8, wherein said chewing gum product comprises a center-fill gum, said center-fill gum comprising a center-fill region and a gum region at least partially surrounding said center-fill region and said casein phosphopeptide-calcium phosphate is located in a region selected from the group consisting of said gum region, said center-fill region and combinations thereof.

11. The chewing gum composition of claim 1, wherein said casein phosphopeptide-calcium phosphate is encapsulated.

12. The chewing gum composition of claim 1, wherein said casein phosphopeptide-calcium phosphate comprises a mixture of said casein phosphopeptide-calcium phosphate in an encapsulated form and said casein phosphopeptide-calcium phosphate in an unencapsulated form.

13. The chewing gum composition of claim 1, wherein said at least one food-grade acid is encapsulated.

14. The chewing gum composition of claim 1, wherein said at least one food-grade acid comprises a mixture of said at least one food-grade acid in an encapsulated form and said at least one food-grade acid in an unencapsulated form.

15. The chewing gum composition of claim 1, wherein said casein phosphopeptide-calcium phosphate and said at least one food-grade acid are encapsulated together.

16. The chewing gum composition of claim 1, wherein said casein phosphopeptide-calcium phosphate and said at least one food-grade acid are encapsulated separately.

17. The chewing gum composition of claim 1, wherein said composition comprises a chewing gum product comprising about 18 mg of said casein phosphopeptide-calcium phosphate and about 20 mg of said food-grade acid.

18. The chewing gum composition of claim 1, wherein said composition provides about 13% tooth remineralization upon mastication.

19. The chewing gum composition of claim 1, wherein said chewing gum composition comprises a chewing gum product displaying a brand or logo that communicates the presence of said casein phosphopeptide-calcium phosphate and said food-grade acid in amounts sufficient to promote remineralization of tooth surfaces.

20. The chewing gum composition of claim 1, wherein said chewing gum composition comprises a chewing gum product displaying a brand or logo that communicates the presence of said casein phosphopeptide-calcium phosphate and said food-grade acid in amounts sufficient to impart acid resistance to tooth surfaces.

21. A method of imparting acid resistance to the tooth surface of a mammal, comprising the steps of:
  (a) applying a chewing gum product into the oral cavity of the mammal, wherein the chewing gum product comprises:
    (i) a gum base;
    (ii) at least one non-sugar sweetening agent;
    (iii) casein phosphopeptide-calcium phosphate in an amount of about 0.5% to about 1.5% by weight of the composition; and
    (iv) at least one food-grade acid in an amount of from about 0.5 to about 2.5% by weight of the composition;
    wherein said composition provides remineralization of enamel in an amount that is at least about 10% greater than the amount provided by a sweetening agent containing chewing gum composition which comprises an equivalent amount of food-grade acid but which is free of casein phosphopeptide-calcium phosphate; and
    wherein said composition provides acid resistance to teeth in an amount that is at least about 4% greater than the amount provided by a sweetening agent containing chewing gum composition which comprises an equivalent amount of food-grade acid but which is free of casein phosphopeptide-calcium phosphate; and
  (b) chewing the chewing gum product for a time sufficient to impart acid resistance to the tooth surface of the mammal.

22. The method of claim 21, wherein said casein phosphopeptide-calcium phosphate is present in amounts of about 0.5% to about 0.769% by weight of said product.

* * * * *